United States Patent [19]

Dupont et al.

[11] 4,454,032
[45] Jun. 12, 1984

[54] FAST FILTERING APPARATUS

[75] Inventors: Yves Dupont, Lans-en-Vercors; Christian Rocher, Jarrie, both of France

[73] Assignee: Commissariat a l'Energie Atomique, Paris, France

[21] Appl. No.: 501,487

[22] Filed: Jun. 6, 1983

[30] Foreign Application Priority Data

Jun. 16, 1982 [FR] France .............................. 82 10498

[51] Int. Cl.³ ............................................ B01D 29/02
[52] U.S. Cl. .................................. 210/96.1; 210/143; 210/324
[58] Field of Search ...................... 210/734, 746, 96.1, 210/141, 143, 148, 266, 316, 324, 325, 329, 446, 455

[56] References Cited

U.S. PATENT DOCUMENTS

| 2,307,318 | 1/1943 | Kinney | 210/324 |
| 3,567,029 | 3/1971 | Quame | 210/266 X |
| 4,224,821 | 9/1980 | Taylor et al. | 210/96.1 |
| 4,388,407 | 6/1983 | Lepain | 210/96.1 |

Primary Examiner—John Adee
Attorney, Agent, or Firm—Pearne, Gordon, Sessions, McCoy, Granger & Tilberry

[57] ABSTRACT

Fast filtering apparatus, particularly for biological liquids.

It comprises in combination:
an injection device equipped with a cylindrical reservoir, whose bottom is sealed by a porous pellet and whose top is sealed by a piston displaceable in translation in the cylindrical reservoir, the latter containing the liquid phase to be filtered;
a filter support device comprising a cylindrical chamber, whose upper part is sealed by a porous pellet serving as a support for the actual filtering material;
a device for bringing about the fast, temporary contact between the injection device and the filter support device;
an electronic control assembly controlling each filtering operation, by simultaneously acting on the contacting device and on the mechanical means for the translation of the piston.

4 Claims, 2 Drawing Figures

FAST FILTERING APPARATUS

BACKGROUND OF THE INVENTION

The present invention relates to a filtering apparatus, enabling said operation to be performed in a minimum of time. This fast filtering apparatus is more particularly applicable to the biological field, particularly to two types of studies widely used in biochemistry and bioenergetics, namely studies of the enzymatic mechanism and measurements of ion flows through cell membranes.

The detailed study of enzymatic reactions, as well as that of the mechanisms controlling ion flows require especially designed and improved equipment, which make it possible to solve the transient events of the investigated process. Usually, the reactions catalyzed by enzymes occur at a very high speed and require methods permitting a time resolution of roughly a few milliseconds. Hitherto, advances in connection with the mechanisms of the enzymatic action have generally followed an improvement in the method used and in particular the time resolution obtained.

Thus, it is known that the duration of an enzymatic cycle is generally well below 1 second. It is generally possible to identify a relatively large number of intermediate states in a cycle. Rapid mixing or multimixing methods have been developed in the past, with a view to investigating these transient states. In principle, these methods are relatively simple, the enzyme E is mixed very rapidly (a few milliseconds) with a molecule or substrate S, the reaction then following its course and is completed during the release of the product P:

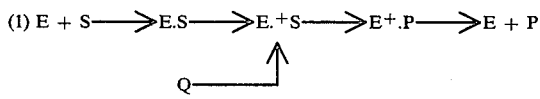

The analysis of the intermediate stages (in this case the state E.+S) is performed by carrying out a second fast mixing (a few milliseconds to a few seconds after the initial mixing) with a reagent Q, which stabilizes E+S. The latter is then analyzed by conventional, but often slow biochemical methods. The enzyme is mixed very rapidly with the molecule or substrate with which it must combine before producing its modification. The object is to investigate the reaction (1).

The enzyme is brought into contact with the molecule to be investigated (or substrate S). In a second stage, the enzyme and the molecule or substrate are combined, followed by the modification of the molecule by the enzyme. The reaction is blocked at this stage with the aid of a reagent Q. Thus, it is possible to analyze the blocked (E+S) by conventional biochemical methods, such as the aforementioned fast mixing.

It is possible to block the reaction at all stages, if there is an appropriate reagent (E+S,E+P, E+P). Another method consists of substituting the natural substrate S for a chemical analog (molecule having the same chemical properties, but special physical properties, which can be optically followed, e.g. fluorescence and absorptivity) making it possible to follow the progress of the reaction (1) as a function of time. The time resolution of fast mixing methods and optical methods is approximately 10 msec.

Ion flow measurements (ion flow=measurement of the flow of molecules, ions, etc entering and leaving a molecule) have in the past almost exclusively been carried out by using filtering methods, e.g. Millipore filters. Briefly, the principle of these measurements is as follows. A suspension of membranous vesicles or cells is diluted in a medium containing the substrate or molecule, whereof it is wished to investigate the ion flow which has to be transported into the cell. Generally, the substrate is labelled by a radioactive isotope. Following an incubation time of varying length, the suspension is filtered. The membranes or cells are held back by the filter and the transport is evaluated by measuring the reactivity of the filter with the aid of a scintillation counter. This method is relatively slow (minimum 2 seconds), but it is the only method which is presently available. It is consequently widely used, because flow measurements are very important in research on the physiology and energetics of cells, as well as in molecular pharmacology.

SUMMARY OF THE INVENTION

The apparatus according to the present invention permits a very fast filtration, which makes it possible to follow the different stages of the reactions within a biological liquid, particularly in biochemistry and bioenergetics.

To this end, the present invention proposes a filtering apparatus comprising:

an injection device equipped with a reservoir, whose bottom is sealed by a porous pellet and whose top is sealed by a piston displaceable in translation in the reservoir by any appropriate mechanical means, said reservoir containing the liquid phase to be filtered;

a filter supporting device comprising a chamber sealed in its upper part by a porous pellet serving as a support for the actual filtering material and connected by its base with pumping means making it possible to produce a vacuum in the chamber;

a device for ensuring the fast and temporary contacting of the injection device and the filter support device;

an electronic control assembly controlling each filtering operation, by simultaneously acting on the contacting device and on the mechanical translation means for the piston and accompanied by the bringing about, at the desired time, of the stoppage of the injection and the disengagement of the injection device and the filter support device.

According to a first embodiment of the invention, the porous pellets are of fritted glass.

According to a second embodiment of the invention, the mechanical means for displacing the piston in translation are constituted by a stepping motor.

Finally, according to the last embodiment of the invention, the device for the rapid, temporary contacting of the injection device and the filter support device comprises a solenoid electrically energized by the electronic control assembly and actuating a lever able to bring about the vertical translation of the filter support by moving it towards or away from the injection device.

BRIEF DESCRIPTION OF THE DRAWINGS

The invention is described in greater detail hereinafter relative to non-limitative embodiments and with reference to the attached drawings, wherein show.

DETAILED DESCRIPTION OF THE INVENTION

Figure 1:
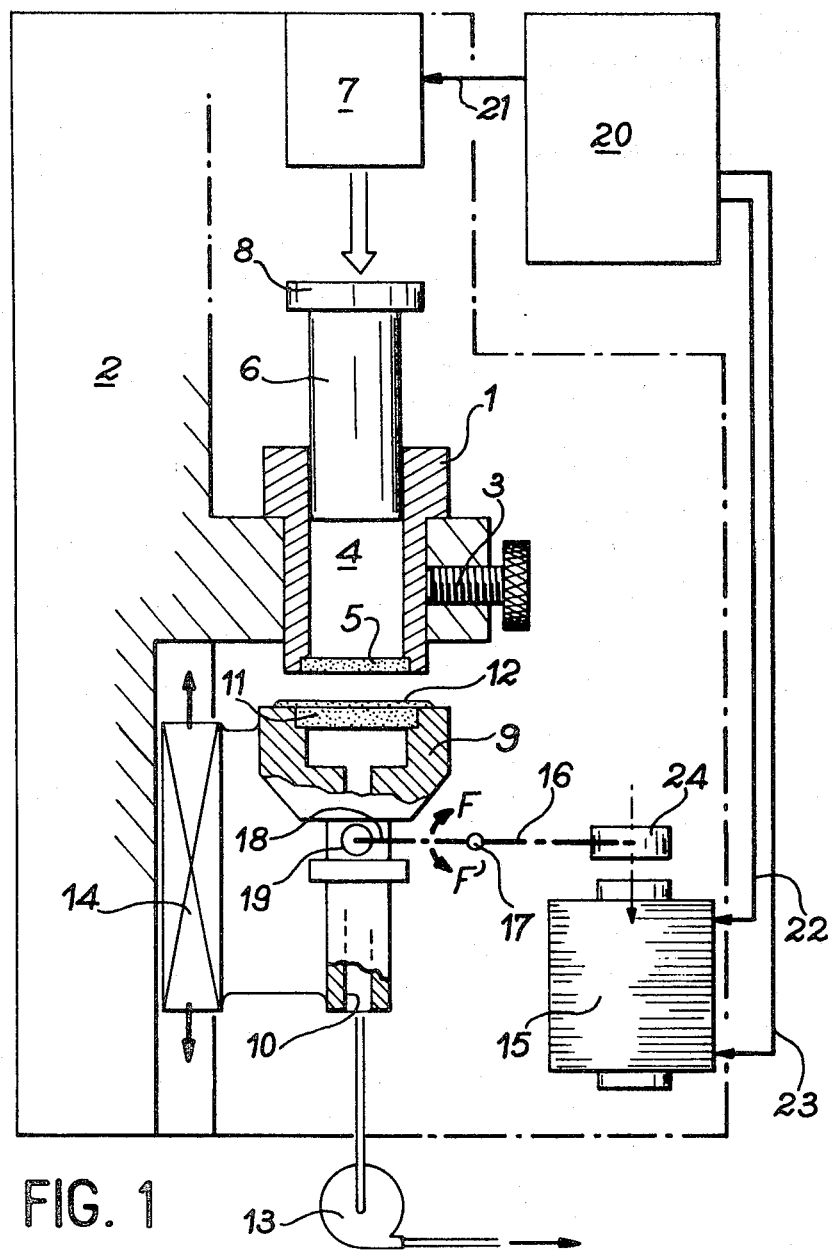
FIG. 1 in elevation, the apparatus according to the invention.

FIG. 1 shows the injection device 1 comprising a cylindrical reservoir 4, whose bottom is sealed by a porous pellet 5 and which is maintained on a support 2 by a fastening screw 3. The upper part of the cylindrical reservoir 4 is sealed by a piston 6, displaceable in vertical translation in cylindrical reservoir 4 and whose displacements are controlled by a stepping motor 7, acting directly on head 8 of piston 6.

The fast filtering apparatus according to the invention, also comprises a filter support device 9, provided on its centre with a cylindrical chamber 10, whose upper part is sealed by another porous pellet 11. Porous pellet 11 acts as a support for the actual filtering material 12 and which is formed in per se known manner by a filter, gel, glass microspheres or any other synthetic support. At the appropriate time, a pump 13 makes it possible to produce a vacuum in cylindrical chamber 10. Per se known translation guidance means 14 make it possible to render the filter support device 9 mobile in axial translation in the axis of injection device 1, under the action of the fast, temporary contacting device 15. Device 15 is able to act remotely, e.g. by electromagnetic action, on a lever 16, which can move about a horizontal spindle 17 and whose end 18 controls, via ball joint 19, the translational movement of the filter support device 9 along its axis. An electronic control assembly 20 permits the simultaneous action by line 21 on stepping motor 7 and by lines 22 and 23 on the rapid contacting device 15.

In the embodiment of FIG. 1, the fast, temporary contacting device 15 comprises a solenoid, electrically energized by the electronic control assembly 20 and able to produce a magnetic field of a sufficient intensity to bring about the attraction of the ferromagnetic armature 24 and the pivoting of lever 16 about its spindle 17, as indicated by arrows FF'.

The operation of the fast filtering apparatus is as follows.

The liquid phase, which it is wished to filter is previously introduced into the cylindrical reservoir 4 of injection device 1. The filtering material e.g. a Millipore filter, is placed on the surface of the porous pellet 11 and the apparatus is then ready to operate. under the action of electronic control means 20, the fast, temporary contacting device 15 of injection device 1 and filter support 9 acts on lever 16, which pivots about its axis 17 causes the fast movement of filter support 9 towards injection device 1, which remains fixed, with the aid of the translation guidance means 14. As soon as contact has been established between the two aforementioned parts of the apparatus, a detector, which is not shown in the drawing, transmits the contact information to control means 20, which by means of line 21 acts immediately on the stepping motor 7, in order to introduce piston 6 into chamber 4 by a predetermined quantity and bring about the very fast filtration of part of the liquid phase contained in chamber 4 through the two porous pellets 5 and 11 and the filtering material 12. At the same time, the pumping means 13 are put into operation by the electronic control assembly 20 and, by producing a vacuum in cylindrical chamber 10, help to speed up the filtration, as well as the evacuation of the liquid phase which has passed through the filter.

At the end of a predetermined time, or as soon as the desired liquid phase quantity has been filtered through the fast filtering apparatus, control assembly 20 acts in the reverse direction on the temporary contacting device 15, in order to again separate the two halves of the apparatus constituted by injection device 1 and filter support 9. This manner of proceeding makes it possible, particularly when the product to be filtered is radioactive, to limit to the strict minimum, the filter contamination time.

As an example, a description will now be given of an application of the fast filtering apparatus according to the invention.

Proteins or membraneous vesicles (nerve or muscle membrane fragments) are placed on a Millipore filter having appropriate characteristics for holding them back after eliminating the excess water. The filter containing the biological matter (membranes or proteins) is then rapidly washed with a solution containing the radioactive substrate, i.e. the molecule which is to be bonded with the proteins or membranes blocked on the filter. The reaction with the molecule or substrate and its exchange with the filtering medium continues throughout the filtration time. Filtration is stopped at the desired instant and the filter is separated from the reagent, the radioactivity contained in the filter being measured and making it possible to obtain information on the state of the reaction at the time of stopping filtration. The device developed makes it possible to very accurately adjust the liquid passage time, as well as the filtered volume. It has been possible to obtain filtration times as short as a few dozen milliseconds, i.e. a time resolution lower than two orders of magnitude compared with that obtained with conventional filtration methods (at least 2 to 5 seconds).

This feature makes the present apparatus of great interest for measuring ion transport through cellular membranes. This also makes it possible to envisage completely original enzymatic kinetic measurements and in particular this apparatus makes it possible to investigate substrate-enzyme complexes or non-covalent molecules. Such a measurement is described in detail hereinafter with reference to a measurement of the kinetics of bonding Ca++ ions to a membranous protein (sarcoplasmic reticulum ATPase-Ca++).

This measurement is performed in the following way:

a Millipore filter (HAWP 0.45 μm) is placed on the filter support;

the membranous vesicles containing the protein are placed on the filter (200 to 300 μg of proteins per filter);

the filter support is placed beneath the injection device, filled with a solution containing $^{45}$Ca;

the reaction is started by the electronic control system, which contacts the filter and the injection device for a predetermined time (between 20 msec and several seconds), during which the injection device is actuated and the solution containing the $^{45}$Ca is injected through the filter (0.2 to 1 ml).

Figure 2:
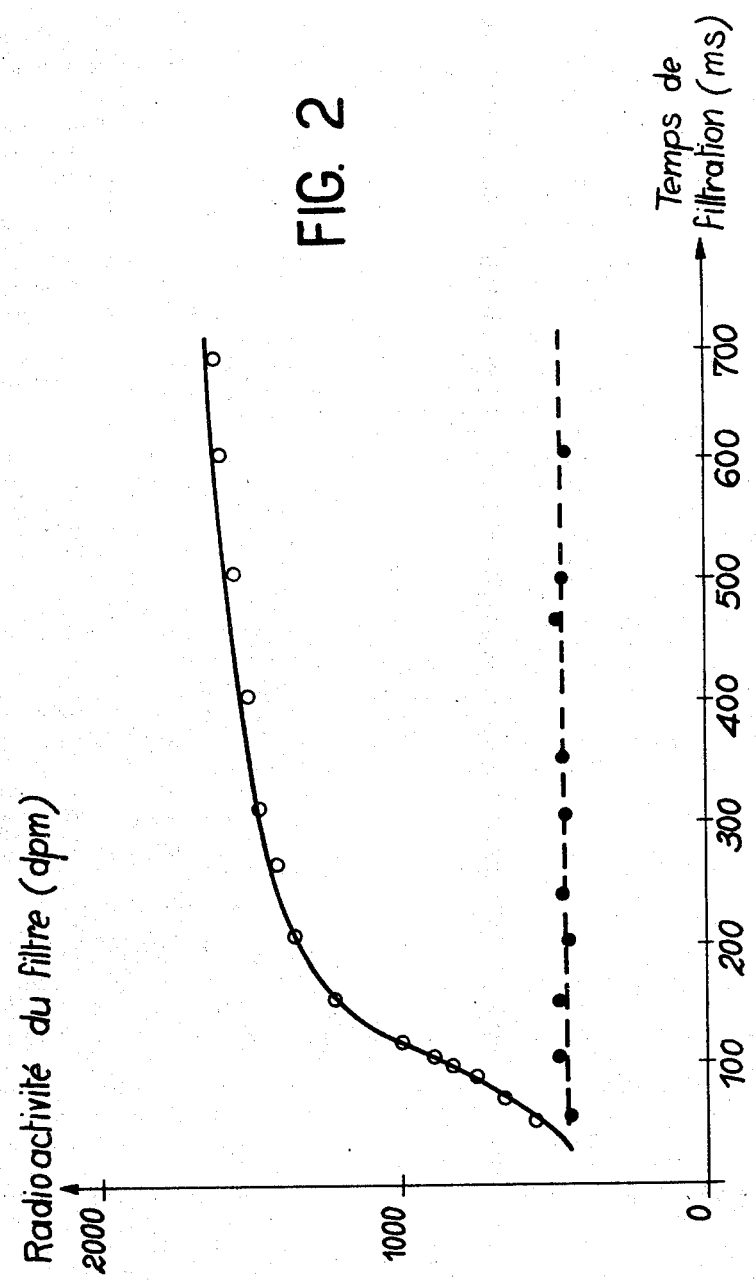
FIG. 2 the measurement of the kinetics of bonding Ca++ ions with a membranous protein.

The filtered liquid quantity is also predetermined. The reaction and filtration are terminated by the physical separation of the filter and the injection device. The radioactivity of the filter is measured with the aid of a scintillation counter. This sequence is repeated for each desired filtration time and the result obtained is the bonding kinetics shown in the following FIG. 2, representing the quantity of $Ca^{2+}$ fixed by the membranous vesicles as a function of the contact time of the latter with the solution of $^{45}Ca^{2+}$. Each point 0 corresponds to a different measurement and consequently each time to a new filter containing the protein to be investigated. The points 0 correspond to measurements carried out with filters not containing protein and consequently correspond to the measurement of the radioactivity trapped in the filter wetting water.

The $Ca^{2+}$ ion bonding kinetics obtained in this series of experiments are then analyzed and this makes it possible to check certain operating details of this protein.

What is claimed is:

1. A fast filtering apparatus, particularly for biological liquids, wherein it comprises in combination:

an injection device equipped with a reservoir, whose bottom is sealed by a porous pellet and whose top is sealed by a piston displaceable in translation in the reservoir by any appropriate mechanical means, said reservoir containing the liquid phase to be filtered;

a filter supporting device comprising a chamber sealed in its upper part by a porous pellet serving as a support for the actual filtering material and connected by its base with pumping means making it possible to produce a vacuum in the chamber;

a device for ensuring the fast and temporary contacting of the injection device and the filter support device;

an electronic control means controlling each filtering operation, by simultaneously acting on the contacting device and on the mechanical translation means for the piston and accompanied by the bringing about, at the desired time, of the stoppage of the injection and the disengagement of the injection device and the filter support device.

2. A filtering apparatus according to claim 1, wherein the porous pellets are made from fritted glass.

3. A filtering apparatus according to claim 1, wherein the mechanical means for displacing the piston in translation comprise a stepping motor.

4. A filtering apparatus according to claim 1, wherein the device for bringing about the fast, temporary contact between the injection device and the filter support device comprises a solenoid, electrically energized by the electronic control assembly and which actuates a lever able to bring about the vertical translation of the filter support, by moving towards or away from the injection device.

* * * * *